United States Patent [19]

Clark

[11] Patent Number: 5,503,741

[45] Date of Patent: Apr. 2, 1996

[54] DIALYSIS DEVICE WITH HERMETICALLY SEALED VACANT CHAMBER

[75] Inventor: Carl Clark, Rockford, Ill.

[73] Assignee: Pierce Chemical Company, Rockford, Ill.

[21] Appl. No.: 395,158

[22] Filed: Feb. 27, 1995

Related U.S. Application Data

[63] Continuation of Ser. No. 125,128, Sep. 22, 1993, abandoned.

[51] Int. Cl.$^6$ .................................................. B01D 61/30
[52] U.S. Cl. .......................................... 210/232; 210/644
[58] Field of Search .......................... 210/321.6, 321.61, 210/32.72, 321.75, 321.84, 232, 500.21, 644; 422/101, 102, 104

[56] References Cited

U.S. PATENT DOCUMENTS

| | | |
|---|---|---|
| 1,757,364 | 5/1930 | Heibig . |
| 1,777,057 | 9/1930 | Urbain . |
| 2,758,083 | 8/1956 | Van Hoek et al. . |
| 3,459,176 | 8/1969 | Leonard . |
| 3,679,059 | 7/1972 | Wyatt et al. . |
| 3,696,931 | 10/1972 | Hough . |
| 4,828,706 | 5/1989 | Eddleman ................................ 210/644 |
| 4,865,813 | 9/1989 | Leon ....................................... 422/101 |
| 5,185,048 | 2/1993 | Guerif ................................. 210/321.75 |
| 5,324,428 | 6/1994 | Flaherty .................................. 210/644 |
| 5,342,517 | 8/1994 | Kopf ....................................... 210/232 |

*Primary Examiner*—John Kim

[57] ABSTRACT

A device for the dialysis of a sample. The device embodies a hermetically sealed sample chamber formed by a gasket with dialysis membranes affixed to each side in substantially parallel relationship. The gasket is impermeable to the sample being dialyzed, but is penetrable and reusable such that a needle or the like can be inserted through the gasket into the chamber and then withdrawn without sample being permitted to leak. The gasket is of sufficient thickness to accommodate insertion of a needle. In a further embodiment, the device is fitted into a rigid housing containing windows exposing the dialysis membranes and further containing a channel parallel to the dialysis membranes for directing a needle into the gasket in a direction substantially perpendicular to the edge of the gasket so that the needle can access the chamber without contacting the surfaces of the membranes.

7 Claims, 2 Drawing Sheets

DIALYSIS DEVICE WITH HERMETICALLY SEALED VACANT CHAMBER

This application is a continuation of Ser. No. 08/125,128, filed Sep. 22, 1993, now abandoned.

FIELD OF INVENTION

The present invention relates to a device for the dialysis of small, fixed-volume samples such as those commonly dialyzed in the research laboratory. The device, which can be disposable, offers convenience in loading and unloading of sample and offers accelerated dialysis of sample. The device can be submerged and moved freely in dialysate held in a vessel of the user's choice such as a beaker.

BACKGROUND

It has been known for some time that molecules of various molecular weights can be separated across a semi-permeable membrane. The membrane by virtue of its composition, and consequently its porosity, allows molecules equal to or less than a particular molecular weight to cross the membrane. Larger molecules are unable to cross. This has led to four common applications of dialysis membrane: 1) exchanging one sample buffer for another buffer, 2) sample desailing, 3) molecular separations, and 4) sample concentration. These applications are most often utilized in the area of laboratory research and the dialysis of patient bodily fluids such as blood.

Various methods have been developed so that dialysis membrane is the sole pathway of molecular exchange between a sample and dialysate. The most widely used method in the research laboratory is taking the dialysis membrane which is molded in the shape of a tube and tying, or clamping, one end of the tube to form a sack. The sample solution is added to the interior of the dialysis membrane sack which is then tied or clamped at the other end which had remained open. The sack, now a closed vessel, is submerged into the dialysate.

The method described above has significant drawbacks. The tying or clamping of the ends of the dialysis membrane tubing requires skill. If the end of the tubing is not carefully tied, the sack will leak and the sample can be lost. Also, it is difficult to load and unload the sample from the sack because the membrane is flaccid; samples are often spilled during these steps. Touching the dialysis tubing membrane with fingers can also effect the sample dialysis. Therefore it requires skill to touch as little of the membrane as possible when tying or clamping it. An alternative is to wear gloves, however, it also requires skill to tie the tubing while wearing gloves. Since the sample chamber of the dialysis tubing membrane is open during the loading and unloading of sample, the sample can be contaminated with any substance in the environmental air. It would be desirable to have a sample chamber which is hermetically sealed and to add the sample with a device such as a needle and syringe. Also, wetted dialysis membrane tubing can not be labeled so labeling must be written on a small clamp or on an object which is inconveniently attached to the tubing with material such as string.

In order to address some of the problems with loading sample into and unloading sample from dialysis tubing as described above, one company has offered commercially preformed dialysis sacks. These sacks are dialysis tubing which has already been clamped at one end and at the open end a funnel has been attached. After the sample is loaded through the funnel, the tubing is clamped below the funnel and dialysis proceeds. Although the loading and unloading of sample are somewhat simplified, the product still suffers the other problems as described above for dialysis tubing.

Another commercially available product has taken another approach to addressing some of the inconvenience of the dialysis tubing and the pre-formed dialysis tubing sack. Two concentric rings, one larger than the other, trap a sheet of membrane between the rings when the outer ring is tightened upon the inner ting. A vessel is formed such that the rings form the walls of the vessel and the floor is the dialysis membrane. The vessel then is floated on top of the dialysate and sample is added to the interior of the floating vessel. Although this solution offers advantages, it introduces new problems. First, the sample is open to the environmental air which allows it to be easily contaminated. Secondly, because the vessel is open, it is easy for the sample to spill into the dialysate as it floats. Loading and unloading are greatly simplified, but assembly of the device requires some skill by the user.

Various patents have issued for the dialysis of patient bodily fluids. For example, U.S. Pat. No. 3,459,176 describes a device for the dialysis of human blood. The invention embodies an inner chamber which dialyzes with dialysate which is contained within a rigid and fixed outer chamber. The inner chamber, or sample chamber, is open on both ends which allows it to be extended by tubing and joined to the patient's circulatory system for dialysis with the dialysate. This device does not allow the sample chamber to be moved from the fixed dialysate vessel to another dialysate vessel. Also, since the sample chamber is designed to be made continuous with the patient's circulatory system the chamber does not accommodate a small, fixed-volume sample such as that used in the research laboratory.

A similar flow system to that described above is shown by Wyatt et al. in U.S. Pat. No. 3,679,059 as a gasket separator unit for membrane packs and a process for the preparation of same. The device embodies a mesh lattice which is embedded a the edges with gasket-like material to form a unit. These units are then stacked in multiples to form a pack. Dialysis, or similar, membranes are fixed between the mesh lattices during the formation of the pack and are accessed through ports in an arrangement described in U.S. Pat. No. 2,758,083. The result is a series of chambers that are fixed in relation to each other and contain alternately sample and dialysate as initially described by Heibig in U.S. Pat. No. 1,757,364. Both the sample and dialysate flow through the series of chambers in opposite directions in order to realize dialysis of both solutions in their enshrines. The sample chamber can not move freely within a dialysate vessel of the user's choice or be easily transferred to another dialysate vessel. This makes the membrane pack impractical for the dialysis of small, fixed-volume research samples.

Urbain described in U.S. Pat. No. 1,777,057 a system for the dialysis of putrescible liquids which practices a fixed-volume sample chamber and a sealed dialysate vessel. This is achieved by placing the putrescible liquid in a sample chamber and floating the sample chamber within a sealed outer vessel which contains the dialysate. The sealed dialysate vessel is ganged in conjunction with other vessels which allow only the introduction of oxygen-free nitrogen gas. Although Urbain practices the use of a sealed dialysate vessel, for use in the research laboratory it would be desirable to have a sealed sample chamber. This would allow the sample being dialyzed to easily be moved freely from one dialysate vessel to another, or to easily change the dialysate within the outer vessel.

Another device has been described by Leon (U.S. Pat. No. 4,865,813) which embodies a sample chamber for a fixed volume sample. Leon shows a sealed sample chamber with a septum for the introduction of sample into a sample chamber with a needle and syringe. Surrounding the sample chamber are four fixed reagent chambers which are communicable with the sample chamber in the center. Molecules from the sample chamber can diffuse into the four chambers, containing four different reagents, resulting in separate colorimetric reactions based on the presence of unknown analyte being analyzed. Since the reagent chambers are presealed for storage, the device is not practical for dialysis of samples such as those dialyzed in the research laboratory. The dialysate chambers are not only in a fixed geometry to the sample chamber, but they are of fixed volume which is not accessible for the addition of fresh dialysate.

U.S. Pat. No. 3,696,931 describes a device which is used for the purification of sea water or water containing impurities. The invention embodies a closed chamber. The closed chamber contains matter which is used to draw water osmotically through a semipermeable membrane leaving contaminants out. The chamber is not hermetically sealed and sample cannot be loaded and unloaded with a device such as a needle and syringe.

Of the devices described above, none permit the convenient loading and unloading of small, fixed-volume samples to be dialyzed in the research laboratory. Also, none protect the sample from contamination during loading and unloading.

SUMMARY OF THE PRESENT INVENTION

The current invention relates to a device for the dialysis of a sample. The device embodies a hermetically sealed sample chamber formed by a gasket with dialysis membranes affixed to each side in substantially parallel relationship. The gasket is impermeable to the sample being dialyzed, but is penetrable and reusable such that a needle or the like can be inserted through the gasket into the chamber and then withdrawn without sample being permitted to leak. The gasket is of sufficient thickness to accommodate insertion of a needle.

In a further embodiment, the device described above is fitted into a rigid housing containing windows exposing the dialysis membranes and further containing a channel parallel to the dialysis membranes for directing a needle into the gasket in a direction substantially perpendicular to the edge of the gasket so that the needle can access the chamber without contacting the surfaces of the membranes.

DESCRIPTION OF THE PREFERRED EMBODIMENTS

Figure 1:
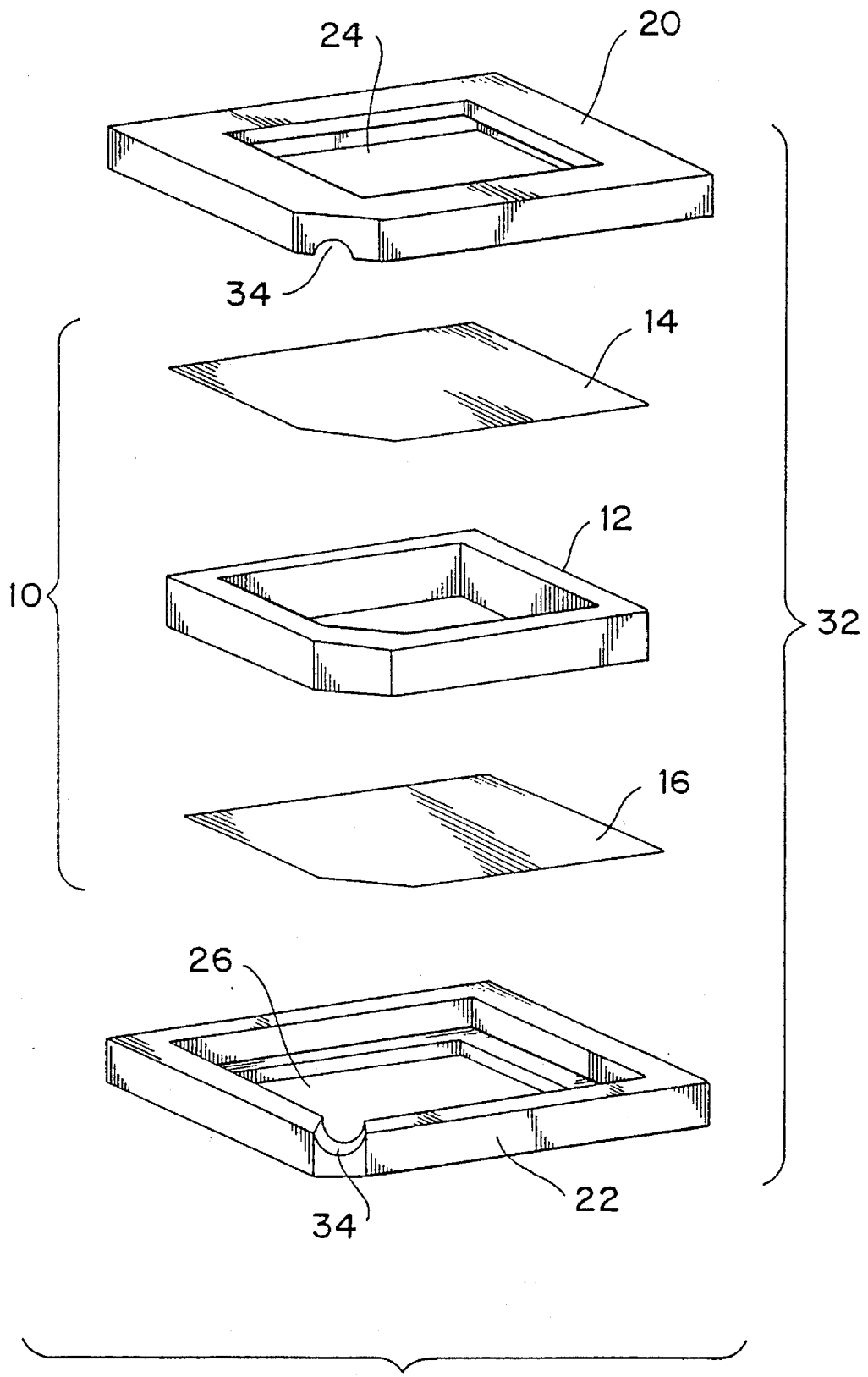
FIG. 1 is an exploded perspective view showing, in disassembled relationship, the device.
Figure 2:
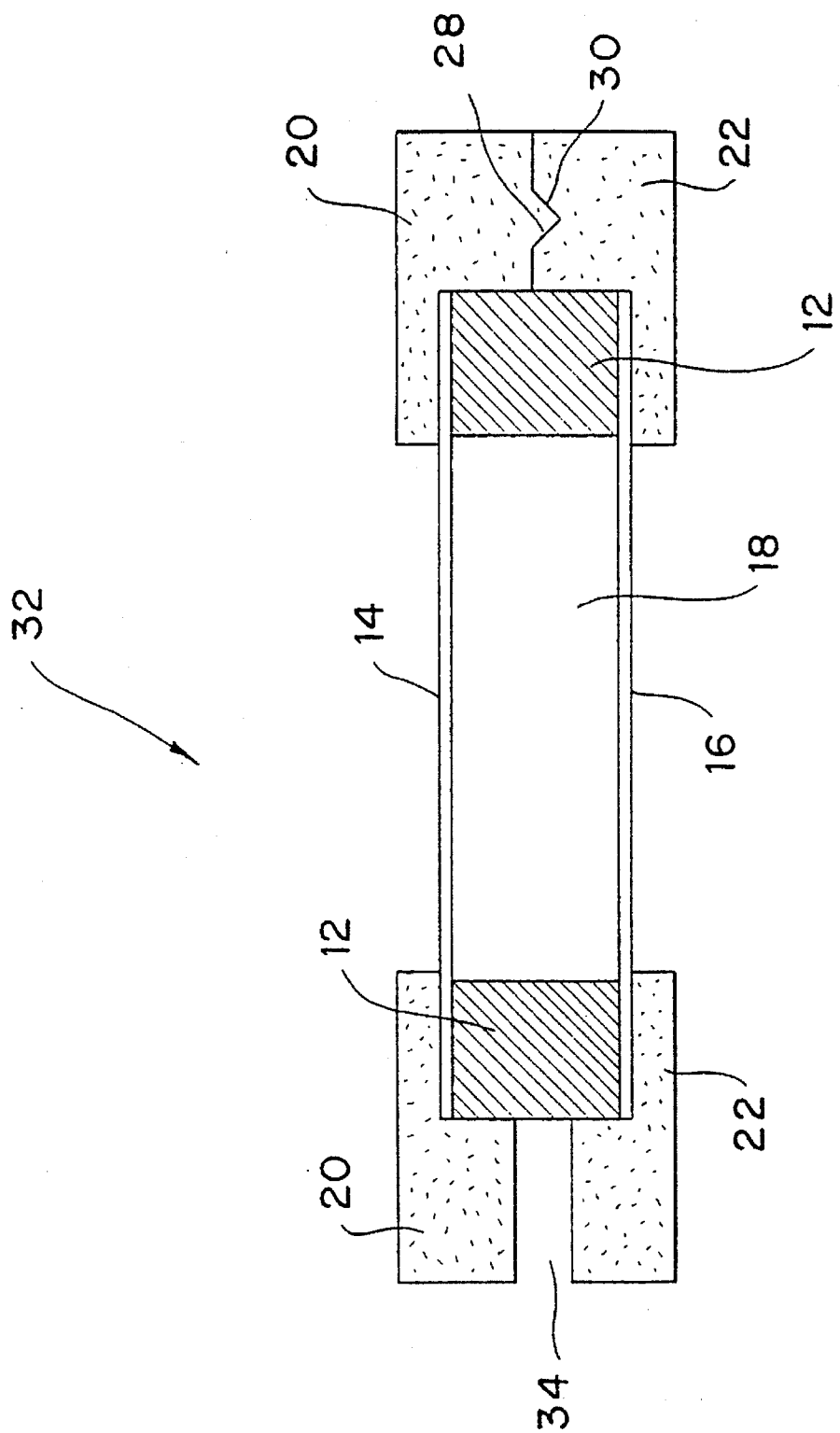
FIG. 2 is a cross-sectional side view of the device.

Turning to the drawings, FIG. 1 illustrates a device 10 depicting the elements thereof is disassembled relationship. The device includes a gasket 12 and dialysis membranes 14 and 16. As illustrated in FIG. 2, in assembled form the dialysis membranes 14 and 16 are affixed to each side of the gasket 12 to form a chamber 18.

An important aspect of the present invention is that the chamber 18 formed by the membranes and gasket be hermetically sealed and that the gasket be penetrable by a needle and resealable. A needle or the like can then be inserted through the gasket into the chamber for delivery of sample and then withdrawn without sample being permitted to leak. To this end the gasket should be a material that is pliable with high memory function. Silicone is most useful. Turning to the membranes, customary dialysis membranes, commonly derived from regenerated cellulose, are useful. In order to achieve a hermetically sealed chamber, the membranes are securely affixed to the gasket by adhesive bonding.

While the device described above, comprising the hermetically sealed chamber 18 formed by the gasket 12 and membranes 14 and 16, can be directly used for dialyzing a sample, preferably the device is fitted into a rigid housing. The housing structurally stabilizes the device for facilitating handling, permits affixing identifying indicia and, perhaps most importantly, allows for directed needle insertion to minimize the probability of needle penetrations through the membrane.

Accordingly, as illustrated in the drawings, a further embodiment of this invention comprises the device 10 fitted into the housing formed by the plates 20, 22. Each of the plates 20, 22 contain windows 24, 26, respectively, positioned opposite the membranes of the device 10. Alignment of the plates 20, 22 can be achieved through a tongue 28 and groove 30 arrangement. The plates can be sealed so as to firmly sandwich the device within housing to form the completed assembly 32 by means of sonic welding, adhesive or the like.

As illustrated, the housing, when assembled, contains a channel 34 for directing and guiding a needle into the gasket and, in turn the chamber. The channel runs parallel to the membranes and is substantially perpendicular to the edge of the gasket so that the needle can access the chamber 18 without contacting the surfaces of the membranes. Preferably, as shown in FIG. 1, the channel meets the edge of the gasket at a corner so that, by tilting the assembly, sample can be collected in the corner and withdrawn. Multiple channels through the housing can be utilized as well.

An example of the use of the device described above would be the exchange of a buffer, in which a protein sample resided, for another buffer. The protein in buffer "A" would be injected into the hermetically sealed sample chamber of the device and, then, the device would be submerged into buffer "B" (dialysate) which is contained in a vessel such as a beaker. The protein being larger than the dialysis membrane pores would be retained within the sample chamber, while the buffer molecules within the sample chamber would exchange by diffusion with the buffer molecules in the dialysate.

The device described herein is easily handled by the user and requires no special skill. Samples are loaded and unloaded with a needle and syringe and during the process fingers never come in contact with the membrane only the housing surrounding the membrane. Since the device is rigid and hermetically sealed, the spilling of sample is improbable. Also, since the sample chamber is hermetically sealed, and the sample loaded and unloaded with a needle and syringe, the sample cannot be contaminated with any substance in the environmental air. The housing surrounding the sample chamber is of ample size which allows for the easy labeling of the sample with commonly used scientific marking pens. The rigidity of the housing of the current invention positions the membranes so that they are parallel to each other and separated only by the thickness of the gasket. The result is a sample chamber which has a high surface to volume ratio. Compared to dialysis tubing which assumes a cylindrical shape when loaded with sample, the higher surface to volume of the current invention results in faster dialysis times.

In use, the sample is loaded into the device by sliding a needle through a needle guide channel, in the housing, through the side of the gasket wall, which also serves the function of a self-sealing septum. Once the needle passes through the gasket wall and penetrates the sample chamber, the plunger of the syringe is depressed and the sample transferred from the barrel of the syringe into the device sample chamber. To effectively execute the dialysis it is preferable to remove any air that was in the chamber before the sample was loaded. The plunger of the syringe can be pulled back to pull the air through the needle which is positioned so that it is in direct contact with the air bubble in the sample chamber. Once the air is removed and the sample is in contact with the maximum amount of dialysis membrane, the device is submerged into the dialysate. The dialysate is held in a vessel such as a beaker and mixing of the dialysate can be incorporated to insure a fresh molecular layer of dialysate in contact with the device membrane. Because of the devices self-contained nature it can easily be transferred to a vessel containing fresh dialysate which has the effect of accelerating the dialysis. Alternatively, the device can be pulled from the dialysate while it is poured from the vessel and fresh dialysate added. After the dialysis of the sample is complete the device is removed from the vessel containing the dialysate and the needle slid through the needle guide channel, in the housing, through the side of the gasket wall. When the needle has passed through the gasket and makes contact with the sample, the plunger is drawn back so that the sample is drawn into the syringe barrel. The needle is positioned in the sample chamber so that all sample feeds into the needle and sample recovery is essentially complete.

What is claimed is:

1. A device for the dialysis of a sample comprising a hermetically sealed vacant chamber formed by a gasket with dialysis membranes disposed on each side of said gasket in substantially parallel relationship without any additional supporting structure there between, said gasket being impermeable to the sample being dialyzed, but penetrable and of sufficient thickness such that a needle can be inserted through the gasket into the chamber, said gasket also having a high memory function such that it is resealable to permit needle withdrawal without sample leakage.

2. A device for the dialysis of a sample comprising a hermetically sealed chamber formed by a gasket with dialysis membranes disposed on each side of said gasket in spaced apart face-to-face relationship without any additional supporting structure there between, said gasket being impermeable to the sample being dialyzed, but penetrable and of sufficient thickness such that a needle can be inserted through the gasket into the chamber, said gasket also having a high memory function such that it is resealable to permit needle withdrawal without sample leakage.

3. A device for the dialysis of a sample comprising a rigid structure housing a gasket with dialysis membranes disposed on each side of said gasket in spaced apart face-to-face relationship without any additional supporting structure there between and forming a hermetically sealed chamber, said rigid structure containing windows exposing the dialysis membranes and means for directing a needle into the gasket so that the needle can access the chamber without contacting the surface of the membranes, said gasket being impermeable to the sample being dialyzed, but penetrable and of sufficient thickness such that a needle can be inserted through the gasket into the chamber, said gasket also having a high memory function such that it is resealable to permit needle withdrawal without sample leakage.

4. The device of claim 3 wherein the dialysis membranes are in substantially parallel relationship.

5. The device of claim 3 wherein said means for directing a needle is a channel.

6. The device of claim 5 wherein the channel is substantially parallel to the membranes and directs said needle into said gasket in a direction substantially perpendicular to the edge of the gasket.

7. The device of claim 6 wherein the dialysis membranes are in substantially parallel relationship.

* * * * *